United States Patent [19]
Fuerholzer et al.

[11] Patent Number: 5,902,750
[45] Date of Patent: May 11, 1999

[54] TAGGING OF WATERBORNE COMPOSITIONS WITH OIL-SOLUBLE MARKERS

[75] Inventors: James J. Fuerholzer, Crystal Lake, Ill.; Alejandro Zimin, Sr., Wayne, N.J.; Peter A. Caputo, South Orange, N.J.; James J. Baluyut, Hoboken, N.J.

[73] Assignee: Morton International, Inc., Chicago, Ill.

[21] Appl. No.: 08/908,407

[22] Filed: Aug. 7, 1997

[51] Int. Cl.⁶ .................................................. G01N 37/00
[52] U.S. Cl. ................................................................ 436/56
[58] Field of Search .................................................. 436/56

[56] References Cited

U.S. PATENT DOCUMENTS

| | | | |
|---|---|---|---|
| 3,764,273 | 10/1973 | Turner et al. | 436/56 |
| 3,861,886 | 1/1975 | Meloy | 436/56 |
| 4,209,302 | 6/1980 | Orelup | 44/59 |
| 4,659,676 | 4/1987 | Rhyne, Jr. | 436/56 |
| 5,156,653 | 10/1992 | Friswell et al. | 44/328 |
| 5,205,840 | 4/1993 | Friswell et al. | 44/428 |
| 5,306,343 | 4/1994 | Richardson, III et al. | 106/668 |
| 5,324,356 | 6/1994 | Goodwin | 436/56 |
| 5,490,872 | 2/1996 | Friswell et al. | 44/328 |

*Primary Examiner*—Jerry D. Johnson
*Attorney, Agent, or Firm*—Wayne E. Nacker; Gerald K. White

[57] ABSTRACT

A water-immiscible marker is dissolved in polyethylene glycol or other suitable carrier, and the marker so dissolved is added to a waterborne composition which is used as an additive to a waterborne or water processable composition. Subsequently, the marker is either extracted with a non-polar solvent or detected by means of a surface spot test. From the non-polar solvent, the marker is extracted with an acidic aqueous solution or an alkaline aqueous solution, depending upon the marker, and color-developed. Likewise, a surface spot test can detect the presence of the marker by, if necessary, first softening the marked surface to be tested either chemically or by thermal means, and developing a color with a color-developing reagent placed on the exposed surface. Applications can include the marking of paint, coatings, wax emulsions and water soluble/dispersable additives commonly used in water based applications, e.g., cement additives.

12 Claims, No Drawings

— 5,902,750 —

TAGGING OF WATERBORNE COMPOSITIONS WITH OIL-SOLUBLE MARKERS

Tagging of Waterborne Compositions With Oil-Soluble Markers The present invention is directed to tagging a variety of waterborne compositions with non-fluorescing, oil-soluble, water-immiscible markers. Applications include, but are not limited to, tagging of wax emulsions, coatings, paints and water soluble/dispersable additives, such as cement additives.

BACKGROUND OF THE INVENTION

It is well known to tag petroleum fuels with "silent" markers so that the fuels can be identified for tax purposes, source of manufacture, brand identification and dilution adulteration. Such markers are added to the fuels at low levels, typically at levels of 100 ppm or well below, where they are not readily detectable with the naked eye. However, as it is necessary to be able to easily detect the presence of such markers, a simple chemical test must be available for their detection. A typical petroleum marker reacts readily with a reagent, such as an acid, a base, or in the case of markers described in U.S. Pat. No. 4,209,302, the teachings of which are incorporated herein by reference, with acid and a diazotized reagent, to produce a chemical species which is both extractable in an aqueous medium and becomes highly colored through a chromophoric reaction.

The markers in U.S. Pat. No. 4,209,302 have also found a non-fuel use as markers for asphalt additives, as described in U.S. Pat. No. 5,306,343, the teachings of which are incorporated herein by reference. By use of such a marker, it can be determined whether a contractor is actually adding, and in appropriate amounts, the additive which adds substantial life to the asphalt, but which additive is relatively expensive.

For similar reasons, it would be desirable to tag additives commonly used in waterborne or water-processable materials and compositions. Additives in the form of aqueous solutions, dispersions and emulsions, are often added to concrete to improve its water-resistance, strength and long term durability. Hence, it would be desirable to have a tool or means to ensure that the specific additive is, in fact added to the concrete, in certain high liability end-use applications such as concrete structures of bridges or high-rise buildings.

Likewise, a similar liability exists in the paint industry. It would be desirable to have a simple and economic method for brand/manufacturer identification. Paint companies are known to pay-out large sums of money yearly in order to settle paint failure claims. In many cases, the paint manufacturer has no fool-proof method in identifying that it is its paint that has actually failed. Therefore, claims go uncontested and are settled strictly based on receipts which can be easily falsified.

In fact, there may be rationale for tagging and identifying a wide variety of waterborne products, such as adhesives, coatings, sealants, inks and floor finishes. In general, it is desired that the markers be soluble in non-polar solvents and insoluble in water, particularly at generally neutral pH ranges, so that the markers are not leached out of the tagged materials by exposure to aqueous solutions.

Markers, such as those described in U.S. Pat. Nos. 4,209,302; 5,156,653; 5,205,840; and 5,490,872, the techniques of each of which are incorporated herein by reference, are highly effective markers for petroleum fuels and therefore would be desirable to utilize them in waterborne and water-processable systems. However, as such markers are intended to be compatible with oil, in some cases they also tend to be incompatible with water and aqueous media. The markers of U.S. Pat. No. 4,209,302, for example, are incompatible with water, either by themselves or in the form they are usually sold, as a solution in an oil-miscible solvent, such as xylene, plus a fatty acid, such as oleic acid. If such marker/solvent/fatty acid compositions are added to concrete, they could agglomerate and are therefore unsuitable for tagging purposes.

While oil-miscible markers are suitable for tagging hydrophobic materials, such as petroleum fuels; water-miscible markers are generally unsuitable for admixture with waterborne or aqueous-processable systems for tagging material, such as concrete. Because concrete structures are commonly exposed to the elements, water-miscible markers would leach out over time. Accordingly, it is a general object of the present invention to compatibilize hydrophobic markers, of types currently used to tag petroleum fuels, with waterborne compositions, such as concrete additives.

SUMMARY OF THE INVENTION

In accordance with the present invention, oil-miscible, water-immiscible markers are compatabilized with a waterborne composition through an appropriate vehicle, such as an appropriate solvent or an appropriate surfactant(s). The marker tags the waterborne composition and remains as a tag in any dried material produced therefrom, such as set concrete, dried paint, dried adhesive, etc. For identification, the marker is initially extracted, either from the waterborne composition, or from the dried material produced therefrom with a non-polar, water-immiscible solvent. In the case of dried materials, prior mechanical preparation, such as powdering of concrete or dried paint, may be necessary to facilitate extraction in non-polar solvent. Next the marker is extracted from the non-polar solvent with either an acidic aqueous solution or an alkaline aqueous solution, depending upon the chemical formula of the particular marker. In some markers, the acidic or alkaline solution acts as the reagent which produces a chromophoric change in the marker, generally producing a strong color that is easily identified by the naked eye and, at least to some extent, quantitatively measurable by chromophoric measurement techniques. In other markers, the marker is reacted with a reagent, such as a diazo compound, which produces a strong color, the chromophore-producing reagent being included in the extraction medium or added subsequently thereto.

In the case of certain dried materials, particularly clear or lightly colored dried materials, such as dried adhesives and paints, an alternative method of identifying the marker in accordance with the present invention is to "spot test" the material with color-developing reagent; acidic, basic, diazo, etc., as the case may be. To enable the color-developing solution to react with the marker in the tagged material, it may be necessary to soften the surface, either chemically or thermally. In the case of concrete, it is in some cases possible to directly "spot test" the hardened concrete itself by application of a color-developing reagent to its surface which inherently has some porosity.

DETAILED DESCRIPTION OF CERTAIN PREFERRED EMBODIMENTS

Markers useful in the process of the present invention include compounds described in the above-referenced U.S. Pat. Nos. 4,209,302; 5,156,653; 5,205,840; 5,490,872 and phthalein-based markers sold under Morton International's Mortrace® 20164 trademark. However, a wide variety of markers of the type used to tag and identify petroleum fuels can be used to tag and identify waterborne compositions and dried materials, prepared therefrom, using the method of the present invention.

U.S. Pat. No. 5,205,840 describes markers of the formula:

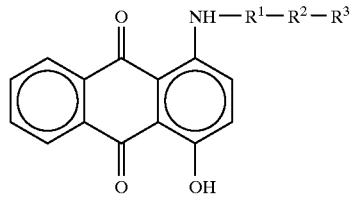

where $R^2$ and $R^3$ are the same or different and are either H or O—($C_1$–$C_3$ alkyl). Such dyes are sold as Mortrace® Purple. These dyes can be identified by reaction with a base, such as KOH, dissolved in an aqueous medium, preferably in the presence of a water-soluble organic co-solvent.

U.S. Pat. No. 5,156,653 describes markers of the formulae:

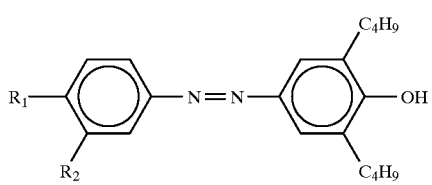

wherein the $R_1$s and the $R_2$s are the same or different and are each selected from H and $C_{1-7}$alkyls, provided that at least one, and prefereably both $R_1$s are a $C_{3-7}$ alky, and provided that the $R_3$s are the same or different and are selected from H, $NO_2$, Cl, Br, F, CN, and Me, and provided that at least one $R_3$ is selected from $NO_2$, Cl, Br, F and CN. These markers can be identified by extraction with an aqueous solution of a water-soluble amine and preferably with an organic co-solvent. These markers are sold as Mortrace® "S" family markers.

U.S. Pat. No. 5,490,872 describes markers of the general formula:

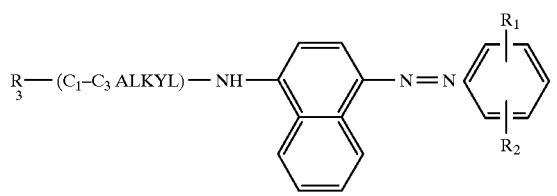

where $R^1$ and $R^2$ are the same or different and are selected from methyl, ethyl, methoxy, halogen, cyano, and nitro and $R^3$ is selected from methyl, methoxy, methoxy ethoxy, and morpholino. These markers are sold as Mortrace® AC and AD markers. These markers are extractable from non-polar solvents with acidic aqueous solutions which protiate the markers, causing them to undergo a chromophoric reaction that produces a strong color.

U.S. Pat. No. 4,209,302 describes markers of the general formulae:

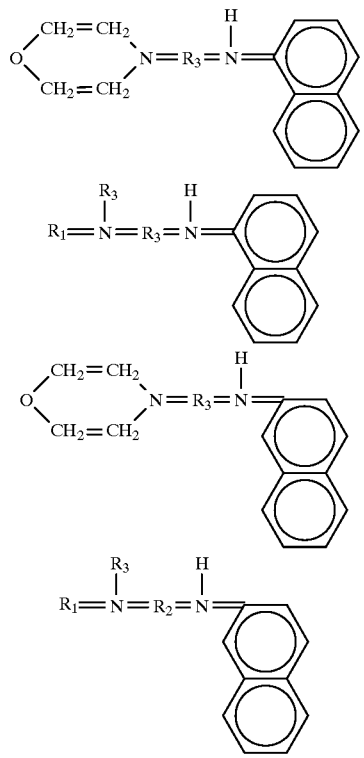

where $R_1$ and $R_2$ are the same or different and are selected from H, and $C_{1-20}$alkyl and R3 is $C_{1-8}$alkyl. These dyes are sold as Mortrace® MP dyes and are identified by extraction with acidic aqueous solution and development with a chromophore-producing diazo compound.

An example of a phthalein based marker is sold as Mortrace® 20164 having the formula:

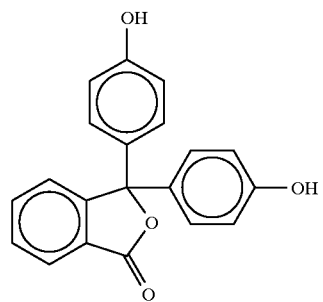

This dye is identified by extraction with a strong base, such as an alkali metal hydroxide solution, which develops a color upon extraction with base.

As described in U.S. Pat. Nos. 4,209,302; 5,156,653; 5,205,840; 5,490,872, such compounds have been previously utilized as petroleum fuel markers, and, as described in U.S. Pat. No. 5,306,343, some compounds have also previously been utilized to tag asphalt additives. Herein, it is discovered that such markers might also be used to tag additives for waterborne systems or tag water-processable products.

Because markers used in accordance with the present invention exhibit good solubility in non-polar solvents and petroleum fuels and are generally incompatible with aqueous media in the absence of strong acid or strong base, an appropriate vehicle is necessary to compatibilize the marker with the aqueous medium such that the marker is homogeneously distributed within the aqueous medium and remains as an integral tag in any dried material produced therefrom. The vehicle may be a solvent in which the marker is soluble, at least at the desired use concentration, and miscible in water, at least to an amount that allows the desired amount of marker solution to mix with the aqueous medium to form a single-phase system and homogeneously distribute the marker throughout the aqueous medium. Currently preferred compatibilizing solvents include polyethylene glycol, such as PEG 200 through PEG 400, diethylene glycol and m-pyrol. Alternatively, non-ionic surfactants, such as ethoxylated nonyl phenol, alkoxylated alkylphenol and long chain fatty acid esters may be used to compatibilize the marker with the waterborne composition. With some waterborne compositions, paint formulations for example, the composition may already contain compatibilizers, such as high levels of surfactants, whereby the markers as solutions in non-polar solvents may be directly added to the compositions.

A particularly preferred compatibilizing solvent is polyethylene glycol. Markers of the above general formulae are soluble in polyethylene glycol to at least about 1.0% up to about 50 gm/100 ml polyethylene glycol at 25° C. Polyethylene glycol is soluble with water at about 100 gm/100 ml. of water at 25° C.; and polyethylene glycol can carry dissolved marker of the above general formulae into water or aqueous medium up to 0.1 wt %, i.e., up to about 1000 parts per million (ppm).

The product to be tagged with the marker, such as paint, typically carries the marker at levels of between about 10 and about 500 ppm. Thus, water/polyethylene glycol/marker solutions may be provided in accordance with the invention that are fairly concentrated in marker relative to the concentration of the marker in the tagged product. Accordingly, a small volume of relatively concentrated water/polyethylene glycol/marker solution may be used to tag a larger volume of product, such as paint or wax emulsion.

The marker may be identified as being present in an aqueous composition, such as a coating; a wet material, such as wet concrete mix; or a dry material, such as dry paint chip or hardened wax emulsion. If tagged material is aqueous or in a liquid form, such as the aqueous media of a coating or the water in a freshly prepared concrete mix, the marker may be extracted from the aqueous medium itself with a non-polar solvent, e.g. xylene. If the tagged material is a dry material, such as dry paint chip or set concrete, the material, e.g. paint chip or concrete, may be powdered, and the marker extracted from the powdered material with a non-polar solvent, e.g. xylene.

If the marker is to be extracted from an aqueous medium, the medium should be, or should be adjusted to be, neutral, and preferably either slightly acidic or basic depending on the chemical formula of the marker (opposite in acidity or alkalinity to the aqueous medium in which the marker will eventually be extracted from the non-polar medium). The markers, prior to reaction with acid or base, as the case may be, have a high affinity for non-polar solvents, such as xylene or toluene, and therefore are readily extracted from aqueous media (that is neutral or opposite in acidity or alkalinity relative to the eventual extracting solution) with non-polar solvents. Likewise, non-polar solvent readily dissolves the marker from dry material, such as dry paint or powdered concrete. Other suitable solvents include, but are not limited to kerosene, 1,1,1-trichloroethane, iso-octane and trichloroethylene.

The marker is then extracted from the non-polar solvent by acidic aqueous or alkaline aqueous solution, as the case may be. In some cases, such as with the markers described in U.S. Pat. No. 5,490,872, an acidic aqueous extracting solution proteates the marker causing it to undergo a chromophoric reaction that produces a strong, easily visible color. In other cases, such as with the markers described in U.S. Pat. No. 5,205,840, an alkaline aqueous extracting solution causes the marker to undergo a chromophoric reaction that produces a strong, easily visible color. In still other cases, an additional color-developing reagent must be added, either contemporaneously with extraction or subsequent to extraction. For, example, the markers described in above-referenced U.S. Pat. No. 4,209,309 are extracted in an acidic aqueous solution, preferably pH 4 or below, and color-developed with a diazo compound.

The volume of acidic or alkaline aqueous solution is sufficient to extract substantially all of the marker, but preferably the volume is as small as is needed so as to concentrate the marker and produce the strongest color. Typically, the ratio of the volume of the aqueous extractant to the volume of the non-polar solvent solution is between about 1:10 and about 1:1, although any ratio may be used, provided the developed color is detectable. For good separation of the aqueous phase from the solvent phase, a minor amount of an anti-emulsifying agent may be added to the extracting solution.

When extracting a dye for which a diazo compound is necessary for color development, the aqueous (generally acidic) extractant may contain a diazo compound or the diazo compound may be added in a separate development step. The diazo compound may be any compound which diazotize the aromatic, e.g., naphthalene, ring of the marker. The diazo compound is provided in stoichiometric excess of any marker which might be present. For convenience of providing test materials with predictable results in the field, it is preferred to use a stabilized diazo compound. Examples of suitable diazo compounds, include, but are not limited to 2-chlor-4-nitro aniline, 2-chlor-aniline, 4-chlor-aniline and 2-nitro-aniline.

The mere fact of color development upon addition of extraction and reaction of the marker with a chromophore-developing reagent is a qualitative test for the presence of the tag and therefore the specified additive. For quantitative testing, spectrophotometric measurements of the color developed is required, and marker level is evaluated against a calibration curve.

In some applications, a surface spot test can easily detect the presence of a marker in a dried material. For instance a spot test is done by first softening the hard uppermost surface of dry paint film and then over-spotted with an appropriate marker reagent to develop a surface color. The upper most surface can be softened by chemical or thermal means. The surface can be heated with a heat gun until soft or a suitable drop of solvent can be put on the surface. Suitable solvents can be, but are not limited to acetone, xylene, and 2-butanone. With concrete, which has substantial inherent porosity, it is sometimes possible to develop color in a tagged specimen merely by applying a chromophore-developing reagent to the surface.

It is known that markers of the above formula may be identified in non-polar liquids, such as petroleum fuels or solvents such as xylene or toluene, at levels as low as about 0.5 ppm. The amount of marker used to tag an aqueous medium is an amount sufficient to conveniently provide at least about 1.0 ppm of the marker to an extracting non-polar solvent; and the amount of marker used to tag concrete is the amount which, in dry materials such as set concrete, can be used to conveniently provide at least about 1.0 ppm of the marker to an extracting non-polar solvent. Typically, an aqueous medium will be tagged with between about 5 and about 500 ppm of the marker. For concrete additives, an appropriate amount of marker is added to the additive in order to detect a developed color in the set concrete.

Identification of the marker can be relatively quantitative, particularly from aqueous media. Relatively quantitative measurements of marker in set concrete or dry paint is also possible, although the heterogeneous characteristics of the materials tend to detract from the accuracy of quantitative measurements.

As noted above, the invention is particularly valuable for identifying marker in a wet concrete mix or dry, set concrete, likewise wet and dry paint. The markers used in the present invention are hydrophobic and will not leach out of set concrete or dry paint over extended periods of exposure to the elements. Thus, if a concrete structure fails long after it has been constructed, it can be determined whether that failure may have been caused, in part, by failure to include the required additives at required levels. Likewise, marking of paints can serve as an easy but accurate means of brand identification and deter fraudulent claims against paint manufacturers. The method of the present invention can also be used to identify marker in waterborne compositions, such as coatings and a variety of other water soluble/dispersable additives.

The invention will now be described in greater detail by way of specific example.

EXAMPLE 1

The water reducible marker, Mortrace® 20155, a 6–7 wt % solution in polyethylene glycol (PEG 400) of Mortrace® MP, described above with respect to U.S. Pat. No. 4,209,302, was stirred into a waterborne, cross-linkable, two-component laminating adhesive system by means of normal laboratory stirring equipment at a level of 1% without any background coloration detected. Prior to the point of application, this adhesive was mixed with an initiator, then coated onto an acetate film with a thickness of 3 mil, using a number 18 wire bound coating bar.

The coated acetate film was then laminated to paper stock and stored under different ambient conditions, (100° F., 32° F. and room temperature), for one week. The laminated samples were then spotted with a suitable diazo compound on the paper side allowing the reagent to absorb through the paper layer and into the marked adhesive coating layer where it causes a bluish pink color generation positively identifying the presence of the water reducible marker.

EXAMPLE 2

The marker, Mortrace® MP, was stirred into a water-based latex interior paint at a concentration of 100 ppm using a typical laboratory stirrer. The presence of this marker even at concentration of upwards of 500 ppm poses no effect on the color or the rheological properties of the paint. In this and other "paint" examples, surfactants which are always present in paint formulations are relied upon to compatibilize the marker.

The marker was extracted by first diluting the paint sample with four times as much water by volume. This accomplishes two things; it makes the paint easier to work with as far as laboratory equipment is concerned, and it helps to reduce the surfactant effects. At this point, the dilute paint was stirred for approximately fifteen minutes with twice as much (by volume) of solvent, i.e., non-polar aliphatic, such as iso-octane or solvents such as kerosene and xylene. A small amount of de-emulsifier was also added.

At this point, the solvent phase contained the marker. It was poured off and filtered using a 11 micron filter in order to remove pigments that can obscure the extraction test. To a separatory funnel, the marker was extracted using fifteen times less extractant than the solvent. The extractant consisted of an aqueous medium of acetic acid and an ammonium salt, such as ammonium chloride. A suitable diazo compound was then added to react the marker. Visually, the extractant phase turned a bluish pink color visible to the eye. This could be spectrophotometrically tested to achieve quantitative results based on a calibration curve.

EXAMPLE 3

Qualitative test for determining MARKER in dried paint 10 grams of dried paint chips, from a paint tagged with 500 ppm Mortrace® 20155 (30–35 ppm active marker), were dissolved in an aqueous solution of 37.5 wt % HCl, 2.5 wt % acetone. The solution was filtered through a Buchner Funnel under vacuum with a #1 Whatman® filter paper. The filtrate was reacted with 2 drops of a suitable diazo compound and shaken for 30 seconds. Development of a magenta color indicated presence of the marker.

EXAMPLE 4

Semi-quantitative test for marke in latex paint

Paint was tagged with 25 ppm Mortrace® MP. 10 gm of the paint was diluted with 100 ml. water. 50% HCl was added to achieve a pH of 1.0. The mixture was filtered through a Buchner Funnel under vacuum with a #1 Whatman® filter paper. The filtrate was reacted with 2 drops of a suitable diazo compound and shaken for 30 seconds, developing a magenta color which is read at 530 nm. The color has a theoretical absorbance of 0.950; however, this can be affected by other colorants in the paint.

EXAMPLE 5

Paint was tagged with 25 ppm with Mortrace® SB, a marker described in above-referenced U.S. Pat. No. 5,156,653. A 31 gram paint sample was diluted with 400 ml. water. 200 ml. iso-octane was added and mixed for 30 minutes. Then 3–5 drops of de-emulsifier were added and the material let stand for 20 minutes. 100 ml. of the iso-octane was isolated, and 5 ml. of Reagent PPHS, an aqueous amine/glycol solution, were added. A bright blue color indicated a positive test result. The color is read at 600 nm. The theoretical absorbance is 0.935; however colorants in the paint can affect this.

EXAMPLE 6

Qualitative test for determining marker in cement

Mortrace® 20155 was added to a concrete mix to provide a calculated 25 ppm based on dry weight of the concrete. 10 grams of the concrete was crushed in a mortar and pestle; rocks and aggregate were removed. 5 grams of the crushed sample was weighed into a 200 ml. beaker. 10 ml. xylene was added to the beaker and the crushed material and xylene mixed for one minute. The xylene solution was filtered into a graduated cylinder. Twice the volume of an acidic aqueous solution, pH<4, was added to the xylene solution in the graduated cylinder. 2 drops of a suitable diazo compound were added to the cylinder and shaken for 30 seconds. A magenta color developed, indicating presence of the marker.

EXAMPLE 7

Paint was tagged with 196 ppm Mortrace® 20164, a phthalein-based liquid marker dissolved in 1-methyl-2-pyrrolidinone, and the paint applied to a substrate. In a test area of the coated substrate, two drops of acetone were applied to soften the coating. One drop of a 50% aqueous sodium hydroxide solution was applied in the area, and in 20 seconds a bright magenta color developed, indicating presence of the marker.

What is claimed:

1. A method of determining the presence of an additive in a waterborne or aqueous processable composition, the method comprising, providing a water-immiscible marker, providing a compatibilizing vehicle which is an organic solvent in which said marker is sufficiently soluble and which solvent is sufficiently soluble in water such that said marker and said solvent form a solution in water in which said marker is present at at least 5 ppm or a non-ionic surfactant which stabilizes said marker in water at at least 5 ppm, tagging said composition by adding said marker to said composition in the presence of said compatibilizing vehicle, obtaining a specimen of purportedly tagged material in either wet or dry state, with a non-polar solvent, extracting said marker from said purportedly tagged material, and concurrently or successively extracting said marker from said non-polar solvent with either an acidic aqueous medium or an alkaline aqueous medium, and reacting said marker with a chromophore-developing reagent to produce a color in said acidic or alkaline aqueous medium.

2. The method of claim 1 wherein said marker is identified from said purportedly tagged material in wet form.

3. The method of claim 1 wherein said marker is identified from said purportedly tagged material in a dry form.

4. A method of determining the presence of an additive in a waterborne or aqueous processable composition, the method comprising, providing a water-immiscible marker, providing a compatibilizing vehicle which is an organic solvent in which said marker is sufficiently soluble and which solvent is sufficiently soluble in water such that said marker and said solvent form a solution in water in which said marker is present at at least 5 ppm or a non-ionic surfactant which stabilizes said marker in water at at least 5 ppm, tagging said composition by adding said marker to said composition in the presence of said compatibilizing vehicle, processing said composition to produce a dry-state material, and applying a reagent to said dry-state material which reacts with said marker to produce a color where said reagent is applied.

5. A method according to claim 4 wherein said dry-state is softened, either thermally or chemically, before said reagent is applied.

6. A method of determining the presence of an additive in a waterborne or aqueous processable composition, the method comprising, providing a water-immiscible marker, providing a compatibilizing vehicle which is a solvent selected from the group consisting of polyethylene glycol, diethylene glycol, and m-pyrol or a non-ionic surfactant, tagging said composition by adding said marker to said composition in the presence of said compatibilizing vehicle, obtaining a specimen of purportedly tagged material in either wet or dry state, with a non-polar solvent, extracting said marker from said purportedly tagged material, and concurrently or successively extracting said marker from said non-polar solvent with either an acidic aqueous medium or an alkaline aqueous medium, and reacting said marker with a chromophore-developing reagent to produce a color in said acidic or alkaline aqueous medium.

7. The method of claim 6 wherein said marker is identified from said purportedly tagged material in wet form.

8. The method of claim 6 wherein said marker is identified from said purportedly tagged material in a dry form.

9. The method of claim 6 wherein said compatibilizing vehicle is polyethylene glycol.

10. A method of determining the presence of an additive in a waterborne or aqueous processable composition, the method comprising, providing a water-immiscible marker, providing a compatibilizing vehicle, tagging said composition by adding said marker to said composition in the presence of said compatibilizing vehicle which is a solvent selected from the group consisting of polyethylene glycol, diethylene glycol, and m-pyrol or a non-ionic surfactant, processing said composition to produce a dry-state material, and applying a reagent to said dry-state material which reacts with said marker to produce a color where said reagent is applied.

11. The method according to claim 10 wherein said dry-state is softened, either thermally or chemically, before said reagent is applied.

12. The method according to claim 10 wherein said compatibilizing vehicle is polyethylene glycol.

* * * * *

UNITED STATES PATENT AND TRADEMARK OFFICE
CERTIFICATE OF CORRECTION

PATENT NO. : 5,902,750
DATED : May 11, 1999
INVENTOR(S) : Fuerholzer et al.

It is certified that error appears in the above-indentified patent and that said Letters Patent is hereby corrected as shown below:

Col. 1, lines 5 - 6: DELETE:
"Tagging of Waterborne Compositions With Oil-Soluble Markers"

Col. 4, lines 1 - 30: The formula should be changed as follows:

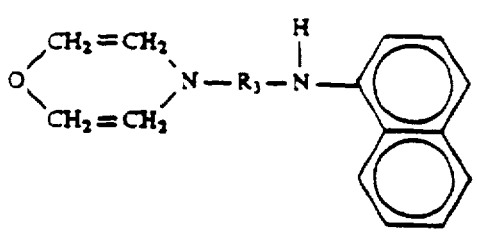

Signed and Sealed this

Twelfth Day of October, 1999

Attest:

Q. TODD DICKINSON

Attesting Officer    Acting Commissioner of Patents and Trademarks